(12) United States Patent
Cheboyina et al.

(10) Patent No.: US 7,413,690 B1
(45) Date of Patent: Aug. 19, 2008

(54) PROCESS AND APPARATUS FOR PRODUCING SPHERICAL PELLETS USING MOLTEN SOLID MATRICES

(75) Inventors: Sreekhar Cheboyina, University, MS (US); John H. O'Haver, Abbeville, MS (US)

(73) Assignee: The University of Mississippi, University, MS (US)

( * ) Notice: Subject to any disclaimer, the term of this patent is extended or adjusted under 35 U.S.C. 154(b) by 113 days.

(21) Appl. No.: 10/977,163

(22) Filed: Oct. 29, 2004

Related U.S. Application Data (60) Provisional application No. 60/515,361, filed on Oct. 29, 2003.

(51) Int. Cl.
*B29B 9/00* (2006.01)

(52) U.S. Cl. .............................. 264/13; 264/14; 425/6; 425/10

(58) Field of Classification Search ........................ None
See application file for complete search history.

(56) References Cited

U.S. PATENT DOCUMENTS

| | | | |
|---|---|---|---|
| 2,570,423 A * | 10/1951 | Batchelder et al. ............ 425/10 |
| 3,060,510 A * | 10/1962 | Fischer et al. .................. 264/9 |
| 4,056,340 A | 11/1977 | Yalkowsky |
| 4,469,648 A | 9/1984 | Ferraris et al. |
| 4,470,202 A | 9/1984 | Buxton et al. |
| 4,829,783 A | 5/1989 | Buchmiiller et al. |
| 5,017,383 A | 5/1991 | Ozawa et al. |
| 5,238,611 A * | 8/1993 | Zamorani et al. ............. 264/13 |
| 5,360,616 A | 11/1994 | Garza Flores et al. |
| 5,387,093 A * | 2/1995 | Takei ............................ 425/5 |
| 5,401,445 A * | 3/1995 | Menchhofer ................. 264/13 |
| 5,437,691 A | 8/1995 | Lauterbach |
| 5,512,303 A | 4/1996 | Garza Flores et al. |
| 5,611,973 A | 3/1997 | Gurfein et al. |
| 5,626,862 A * | 5/1997 | Brem et al. .................. 424/426 |
| 5,633,014 A | 5/1997 | Garza Flores et al. |
| 5,643,604 A | 7/1997 | Angeles Uribe et al. |
| 5,693,342 A | 12/1997 | Cervos et al. |
| 5,694,777 A | 12/1997 | Weyermanns |
| 5,707,636 A | 1/1998 | Rodriguez et al. |
| 5,766,521 A | 6/1998 | Le Thiesse et al. |
| 5,807,584 A | 9/1998 | Thiesse et al. |
| 5,876,754 A | 3/1999 | Wunderlich et al. |
| 6,074,581 A | 6/2000 | Wood et al. |
| 6,077,543 A | 6/2000 | Gordon et al. |
| 6,103,269 A | 8/2000 | Wunderlich et al. |
| 6,132,772 A | 10/2000 | Sherman |

(Continued)

OTHER PUBLICATIONS

Cheboyina, et al.; A Novel Freeze Pelletization Technique for Preparing Matrix Pellets; Pharmaceutical Technology; Oct. 2004; pp. 98-110.

(Continued)

*Primary Examiner*—Mary Lynn F Theisen
(74) *Attorney, Agent, or Firm*—Stites & Harbison PLLC; Richard S. Myers, Jr.

(57) ABSTRACT

A method and apparatus for forming pellets, the apparatus comprising a column for housing column liquid; column liquid; temperature controlling elements engaging the column and capable of maintaining a first and second temperature in the column liquid, and an injection orifice to introduce the liquid pellet composition to the column liquid.

33 Claims, 6 Drawing Sheets

U.S. PATENT DOCUMENTS

| | | |
|---|---|---|
| 6,162,377 A | 12/2000 | Ghosh et al. |
| 6,284,279 B1 | 9/2001 | Vanzin |
| 6,361,298 B1 * | 3/2002 | Kiefer et al. .................... 425/5 |
| 6,365,190 B1 | 4/2002 | Gordon et al. |
| 6,379,707 B2 | 4/2002 | Vladyka, Jr. et al. |
| 2002/0012704 A1 | 1/2002 | Pace et al. |
| 2002/0081335 A1 | 6/2002 | Rodriguez |

OTHER PUBLICATIONS

Cheboyina, et al.; A Mathematical Model to Predict the Size of the Pellets Formed in Freeze Pelletization Techniques: Parameters Affecting Pellet Size; J. Pharmaceutical Sciences; vol. 95, No. 1; Jan. 2006; pp. 167-180.

* cited by examiner

PROCESS AND APPARATUS FOR PRODUCING SPHERICAL PELLETS USING MOLTEN SOLID MATRICES

PRIORITY

This application claims priority to U.S. Patent Application No. 60/515,361, filed Oct. 29, 2003, now abandoned, the contents of which are incorporated herein by reference in its entirety.

FIELD OF THE INVENTION

The present invention relates to a process and apparatus for solidifying molten solid matrices into spherical pellets. The spherical pellets of the present invention may have various applications such as, for example, immediate and controlled release of actives/drugs in pharmaceutical formulations. Immediate and controlled release products are advantageous in situations where there is a desire to obtain different release profiles of the actives.

Other applications for the spherical pellets of the present invention include use in fertilizers, agrichemicals, cosmetics, personal care products, household products, etc.

In embodiments of the present invention, a molten solid carrier/matrix, or pellet composition liquid medium, is introduced into a column of liquid, which is immiscible and inert with respect to the pellet composition liquid medium. The pellet composition medium moves in the liquid column in the form of solidifying liquid droplets as it travels a length of the column. The pellet composition medium can travel through the column either in an upward or downward direction in the column liquid depending on its density with respect to the liquid in the column and/or depending on the current or flow of the column liquid. In embodiments of the present invention, pellets can have a size in the range of sub-micron sizes to about 5 millimeters.

BACKGROUND OF THE INVENTION

Pelletization is the agglomeration of active ingredients and excipients in the form of spherical beads called pellets. With respect to the preferred embodiment of the present invention, pharmaceutical pellets have numerous pharmacokinetic and biopharmaceutical advantages over single dosage units such as tablets. Moreover, they provide a viable alternative for blending incompatible active ingredients, obtaining different release profiles and development of multi-drug controlled release formulations. As a result of these flexibilities, use of pellets in oral drug delivery systems has been growing steadily over last few years and pelletization has become a multi-million dollar industry.

Pellets are prepared on an industrial scale by extrusion-spheronization, high speed shear mixers, drug layering using coating pans and fluidized bed equipment and cryopelletization. All these methods require very specific and expensive equipment and highly skilled staff. In addition, process development and validation of these techniques is a tedious procedure. The present invention presents a simple and new technique for producing pellets with varying properties for multiple commercial uses.

The concept of dropping liquids/molten liquids as droplets into a cooling fluid and thereby freezing/solidifying them into pellets is known in the art. The cooling fluid usually used is typically either a liquid nitrogen or cooling gases from liquid nitrogen. The most widely used process for producing solid particles is called 'spray congealing', where molten solid mass is dropped/sprayed into cooling chambers/cooling towers. This process may not be suitable for solids which have long crystallization temperatures and also for solids which exhibit supercooling like sugars. Accordingly, the height of these prior art towers will need to be high, and they can be as high as 100 meters. Embodiments of the present invention will not require towers of that height. Moreover this prior art process may impart surface irregularities, and the pellets may not be spherical in shape.

In another technique, called 'cryopelletization', aqueous/organic solutions or suspensions or emulsions are dropped into liquid nitrogen to get frozen particles. These particles are further freeze dried/lyophilized to remove water/organic solvents. Liquid nitrogen has a temperature of about −196° C., which is difficult to handle. The droplets which are liquids/semisolids can lose their shape upon impact with the liquid nitrogen, therefore, surface irregularities may be present and they may not be in spherical shape.

U.S. Pat. No. 6,074,581 discloses a method of making prills that comprises injecting a prill-forming composition into a liquid. The liquid is in turbulent flow when the mixture is injected so as to break up the prill mixture into small droplets and to separate them during subsequent cooling and solidification. This turbulent flow makes pellet uniformity more difficult to obtain.

U.S. Pat. No. 4,470,202 describes a method of making spherical pellets comprising introducing a liquid pellet medium into a column liquid in the form of droplets and collecting frozen pellets at the top of a column. The present invention achieves greater flexibility in pellet size control, shape, and size distribution.

The present invention overcomes deficiencies described in the prior art.

SUMMARY OF THE INVENTION

An embodiment of the present invention is a method of preparing a spherical pellet that comprises providing a liquid pellet forming medium; providing a column; introducing the liquid pellet forming medium into a column liquid that is housed in a column, with the column liquid being maintained at a first temperature throughout a first length of the column and being maintained at a second temperature throughout a second length of the column; cooling the pellet forming medium as it travels in the column so that the pellet forming medium solidifies and forms pellets; and separating the pellets from the column liquid.

Another embodiment of the present invention is an apparatus for producing pellets from a liquid pellet composition that comprises column for housing column liquid; first and second temperature controlling elements engaging the column and capable of maintaining a first and second temperature in the column liquid, the first temperature being above or below the solidification temperature of the liquid pellet composition; the second temperature being lower than the first temperature; an injection orifice to introduce the liquid pellet composition to the column liquid; and a collection device for removing pellets from the apparatus.

In another embodiment of the present invention, the above apparatus may comprise a column liquid inlet and a column liquid outlet, which together produce a column liquid flow from the inlet to the outlet.

One aspect of the present invention is to provide a process for solidifying a pellet composition liquid medium to produce solidified spherical particles that includes introducing the pellet composition liquid medium to a column liquid in the form of droplets. At least a portion of the column liquid is maintained at a temperature lower than the solidification temperature of the pellet composition liquid medium. The column liquid should preferably be immiscible with, and inert with the pellet medium.

As is shown in the drawings, in embodiments of the present invention, the liquid pellet medium has a density greater than the column liquid, resulting in the solidified particles sinking through the column liquid and be collected at the bottom of the tower/column. In other embodiments of the invention, the column liquid has the greater density. In these embodiments, the pellet medium is introduced through a nozzle in a lower portion of the tower and the solidifying/solidified pellets float upward to the top of the tower for collection.

In other embodiments, the column liquid is flowing either upward or downward in the tower, which assist the pellets in moving upward or downward for collection.

In aspects of the present invention, pellets made via the apparatus and methods of the present invention can be used in immediate or controlled release pharmaceutical formulations, fertilizer, agricultural formulations, cosmetic formulations, personal care products, etc.

Additionally, peptide and protein drugs can be embedded in the pellet forming material by using low melting solids like PEG 1000 (M.P 37° C.-40° C.), Brijs (30° C.-37° C.), cocoa butter (M.P 30° C.-37° C.), etc. In other aspects of the present invention, soft pellets can be obtained by incorporating hydrophilic liquids into hydrophilic solids matrices. Similarly hydrophobic liquids can be added to hydrophobic solid matrices.

Pellets which are obtained by above methods can be subsequently coated with suitable polymers and can be used in a variety of fields. For example, pharmaceuticals can be used in delayed release and colon specific formulations.

There are various advantages of the present invention over the prior art, which include the formation of pellets that are non-porous and spherically shaped, liquid nitrogen not being required, and freeze drying/lyophilization process not being required. In embodiments of the present invention, pellets obtained are solid at room temperature, and the extraction of actives/drugs is minimum into the column liquids. Additionally, with respect to the present invention there is direct heat exchange when liquids are used as cooling fluids rather than gases, so the length of the columns can be smaller.

With the method and the apparatus of the present invention, pellets are formed by a uniform process. Additionally, the pellets are of uniform size or narrow size distribution. The uniform size and narrow size distribution can be controlled much easier than what is described in the prior art. For example, the droplet released into the column liquid is what becomes the pellet. The pellet size is not determined by particles broken by turbulence, for example. This feature allows more pellet size control by injection volume and pressure.

Finally, the present invention provides a simple, inexpensive and relatively maintenance free technique for producing pellets that are useful in many applications.

DESCRIPTION OF THE INVENTION

The present invention pertains to the concept of immiscibility between molten solids and column liquids. In this method, a pellet composition moves in the liquid column in the form of liquid droplets. The droplets become solidified into spherical pellets as they move though the column. This pellet composition can move either in upward or downward direction in liquid column depending on its density with respect to the liquid in the column. Additionally, if the pellet matrix has approximately the same density as the fluid, the column could be mounted in any direction, including horizontally, as long as the pellet cools before it hits the walls. Thus embodiments of the present invention include a vertical column (±10%), a substantially vertical column (± about 45°), substantially horizontal column (± about 45°), and horizontal columns (±10%). Thus embodiments of the present invention include columns mounted in an angle ranging from 0° to 90°.

The pellet matrix, or pellet composition liquid medium of the present invention is a composition that is useful for solidifying, and may contain a predetermined amount of an active chemical such as, for example, a pharmaceutical, fertilizer, agrichemical, cosmetic, etc.

Besides the chemical and the carrier material the composition to be solidified (i.e., the pellet composition liquid medium) may contain other additional ingredients. For example, when preparing pharmaceutical dosage forms the composition may include pharmaceutically acceptable adjuvants such as coloring agents, flavoring agents, preservatives and the like. In addition the composition may contain ingredients which aid in the dispersion of the chemical. For example, the composition may include a surfactant, e.g. Polysorbate 80 BPC (polyoxyethylene (20) sorbitan monooleate). The composition may also include ingredients such as fillers (e.g. mannitol, sorbitol) which may improve the physical properties of the final pellet product.

Figure 3:
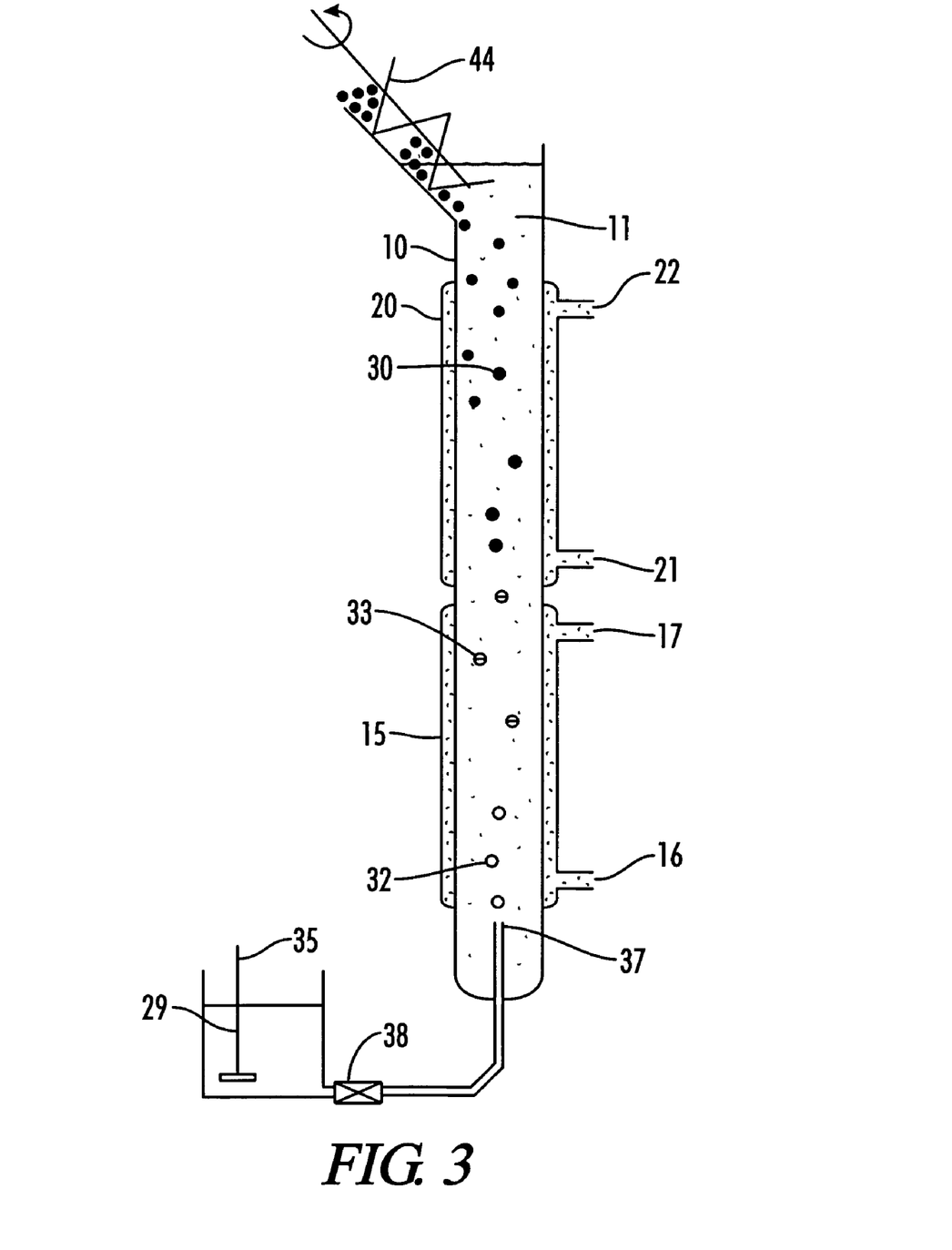
FIG. 3 is a diagrammatic side elevation of an apparatus that may be used in connection with the present invention. In this embodiment, pellets travel upward through the column.

In embodiments of the present invention, a liquid or molten pellet forming composition is introduced into a column of liquid, which is typically immiscible and inert with respect to the molten carrier. The pellet composition moves in the liquid column in the form of liquid droplets, which become solidified into spherical pellets. These molten liquid droplets can move either in upward or downward direction in liquid column depending on their densities with respect to the liquid in the column. For example, if the density of the pellet composition is more than that of the liquid in the column then the droplets are introduced from the top of the column and solidified pellets are collected at the bottom of the column as illustrated with the apparatus of FIG. 1. Alternatively, if the density of the pellet composition is less than that of the liquid in the column then the droplets are introduced from the bottom of the column and solidified pellets are collected at the top of the column as illustrated with the apparatus of FIG. 3.

The orifice used to introduce the pellet composition to the column liquid may, in some embodiments, be a single-hole or single-outlet nozzle or multi-hole nozzle. Furthermore, more than one orifice may be used with an apparatus of the present invention. For example, 2, 3, or 4 nozzles may be used. The orifices may have multiple possible arrangements that allow the droplets to stay separated until they solidify. Typically, multiple orifices will be parallel to one another. Another example of an orifice of the present invention is an atomizer.

The manner in which the pellet medium arrives into the orifice is not known to be critical as long as proper flow of the medium is achieved and maintained. For example, the pellet medium may arrive into a nozzle either by using a pump or via positive air pressure, which may be provided by a gas stream, such as a stream of nitrogen. The orifice may be maintained at a temperature slightly above the melting point of the pellet medium. Additionally, the pellet medium may pass through the nozzle either by a drop wise-type action with no added pressure, to high pressure spraying such as with an atomizer.

The pellet composition may comprise an active chemical compound and a carrier. These carriers are typically solid materials that melt on heating and encapsulate actives/excipients upon solidification. Two examples with respect to the present invention are (a) hydrophilic solids (solids which are soluble in water) and (b) hydrophobic solids (solids which are insoluble in water). The molten solid carrier is chosen in such a way that its melting point is preferably below 100° C. to minimize degradation of actives at elevated temperatures.

The hydrophilic solids include but are not limited to polyethylene glycols (PEGs) (including those with Mw. 1000 or above), polyethylene oxide (PEOs) (including those with Mw. 1000 or above), povidone (PVP) (including those with Mw 2500 or above), polyvinyl alcohol, sugars (including those with low melting point sugars like xylitol etc.), water soluble polyoxyethylene derivatives (Brijs), polyethylene-propylene glycol copolymers(poloxamers), PEG derivatives, PEO derivatives, PEG-PEO derivatives or the combinations of the above.

The hydrophobic solids include but are not limited to glyceryl monostearate, glyceryl palmitostearate, glyceryl dibehenate, cetostearyl alcohol, cetyl alcohol, stearyl alcohol, cholesterol, hydrogenated vegetable oils, phospholipids and its derivatives, lanolin, lecithin, triglycerides, long chain fatty acids/hydrocarbons, hard fat, oil soluble Brijs, cocoa butter, waxes or the combinations of the above.

Actives/excipients may be added as known in the time-release formulation art. Actives are the simple organic/inorganic molecules and proteins and peptides which are therapeutically useful. Excipients include, but not limited to, known release retarding polymers like HPMC, Eudragits etc., polymers which enhance drug release, disintegrating agents. Additionally, molten solid matrices, in which active/excipients are dissolved/dispersed, may be added as known in the art. A matrix can be various combinations of hydrophilic/hydrophobic carriers along with actives/excipients. The amount of dispersed phase can be up to 30-40%.

The column liquids in the column generally are of two types (a) hydrophobic liquids (liquids which are immiscible with water), and (b) hydrophilic liquids (liquids which are miscible with water at all proportions).

Examples of the hydrophobic liquids include, but are not limited to, silicone oils (such as those with viscosities from 1 cst to 100 cst, and those with 5 cst to 50 cst), mineral oil, fixed/vegetable oils, fluorocarbon fluids, aliphatic long chain hydrocarbons or the combinations of the above.

Examples of hydrophilic liquids include but are not limited to liquid polyethylene glycols (liquid PEGs) (such as those with Mw. 200-800), propylene glycol, propylene carbonate, glycofural, glycerin, ethyl alcohol, water or the combinations of the above.

Figure 1:
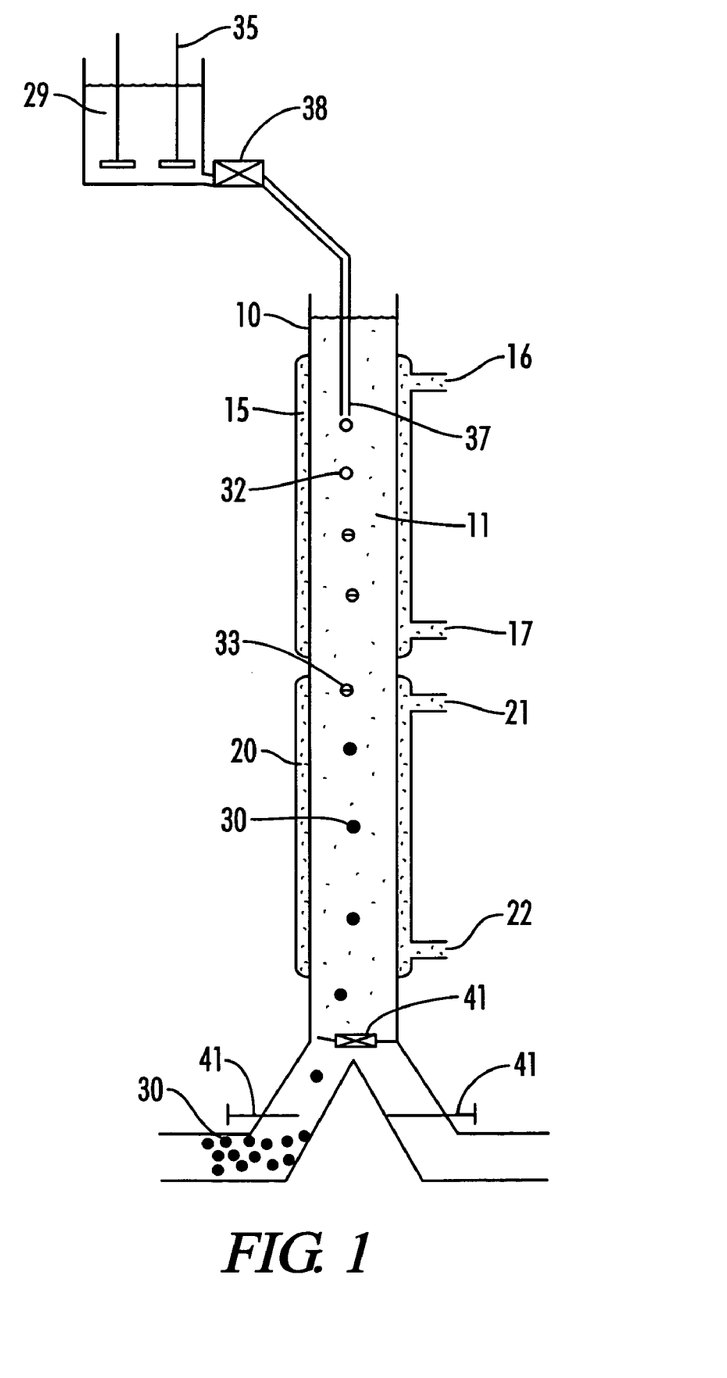
FIG. 1 is a diagrammatic side elevation of an apparatus that may be used in connection with the present invention. In this embodiment, pellets travel downward in the column.

FIGS. 1-4 show embodiments of the present invention. As shown in FIG. 1, an apparatus 10 is for forming spherical pellets 30. The pellet composition medium 29, which may be hydrophilic or hydrophobic or both, is melted. This may be accomplished by using either a water bath or electric heaters and temperature is maintained higher than the melting points of the carrier solids, for example, about 5° C. above melting point. As stated above, actives and/or excipients may be added to the molten mass and stirred well with stirrers 35 to form a uniform pellet composition medium solution/liquid/dispersion 29. The pellet composition may be delivered to the orifice 37 via a pump 38 and introduced into the column liquid 11 using orifices with a suitable gauge size. As indicated above, the pellet size is dependent on the size of the orifice and flow velocity of column liquid.

The orifices 37 can be in any number depending on the desired rate of production of pellets. Again, the orifices can be of the same size or different sizes depending on the range of pellet sizes required. Further the orifices can be static or vibrated electrically. The embodiments shown in the Figures show the nozzles immersed in the column liquid 11. Alternatively, the pellet liquid 29 may be introduced into the column 10 by being dropped into the column liquid 11. The height from which the pellet liquid is dropped can vary. In other embodiments, the pellet liquid can be introduced as droplets or sprayed with an atomizer.

The column 10, where the pellet forming liquid 29 is introduced, is maintained at a first temperature by a first temperature controlling element 15, which may be heated/cooled by a liquid or gas that circulates about a portion of the column through an inlet 16 and an outlet 17. A temperature controlling jacket is shown in the Figures. Additional embodiments include a coil engaging the column. The nature of the temperature controlling element can vary widely, as long as it imparts a temperature on a portion of the column. The temperature controlling element can be, or include a device that injects heated/cooled carrier liquid. This first temperature can range from about 25° C. to about 100° C., depending on the nature of the pellet composition liquid 29. This portion of the column allows the liquid droplets to attain an equilibrium spherical shape as they become a semi-solid spherical mass 32,33. Additionally, this region of the first temperature prevents solidification of the pellet liquid in the orifice 37. In some embodiments, this first temperature may be at or above the solidification temperature of the pellet composition.

As the pellets move further in the column they become more solidified as pellets 30. In the embodiments depicted, significant hardening occurs in the area of a second temperature controlling element 20 that provides a second temperature in this portion of the column. The second temperature controlling element may be the same or different element device as the first temperature controlling element. The second temperature is typically colder than the first temperature. For example, in the area around this temperature controlling jacket, the temperature of the column liquid 11 is maintained between about 10° C. to about −40° C., depending on the nature of the pellet liquid. Various gases or liquids can be circulated through this element via the second element inlet 21 and outlet 22. Additionally, cooling mixtures such as, for example, acetone/dry ice, acetonitrile/dry ice or ice-salt mixtures can be circulated through the cooling element. The length of the first and second portions of the column can vary. Cooling can be accomplished by the cooling element via a variety of means including, but not limited to, cooling jackets, cooling coils, and injection of cooled carrier liquid.

Solidified pellets 30 are collected into collectors. In the embodiments depicted in FIGS. 1 and 2, pellets 30 are collected at the bottom of the column. More than one collector can be used alternatively to provide continuous production of pellets. Multiple valves 41 are used to facilitate the collection step. In the embodiments depicted in FIGS. 3 and 4, pellets 30 are collected at the top of the column 10 and can be removed using any collection mechanism such as, for example, filtration, centrifugation, etc. An example of the collection mechanism is the worm mechanism depicted in FIGS. 3 and 4. Separation can be done by a variety of established methods for separation particulates, including filtration, centrifugation, etc.

Pellets obtained from the apparatus and process of the present invention may be washed after collection. This washing may occur with a suitable solvent such as alcohol, ether, or water to remove liquids from surface of the pellets. Additionally, collected pellets may be dried in vacuum at about 25° C. for up to about 24 hrs to remove any residual solvents.

Figure 2:
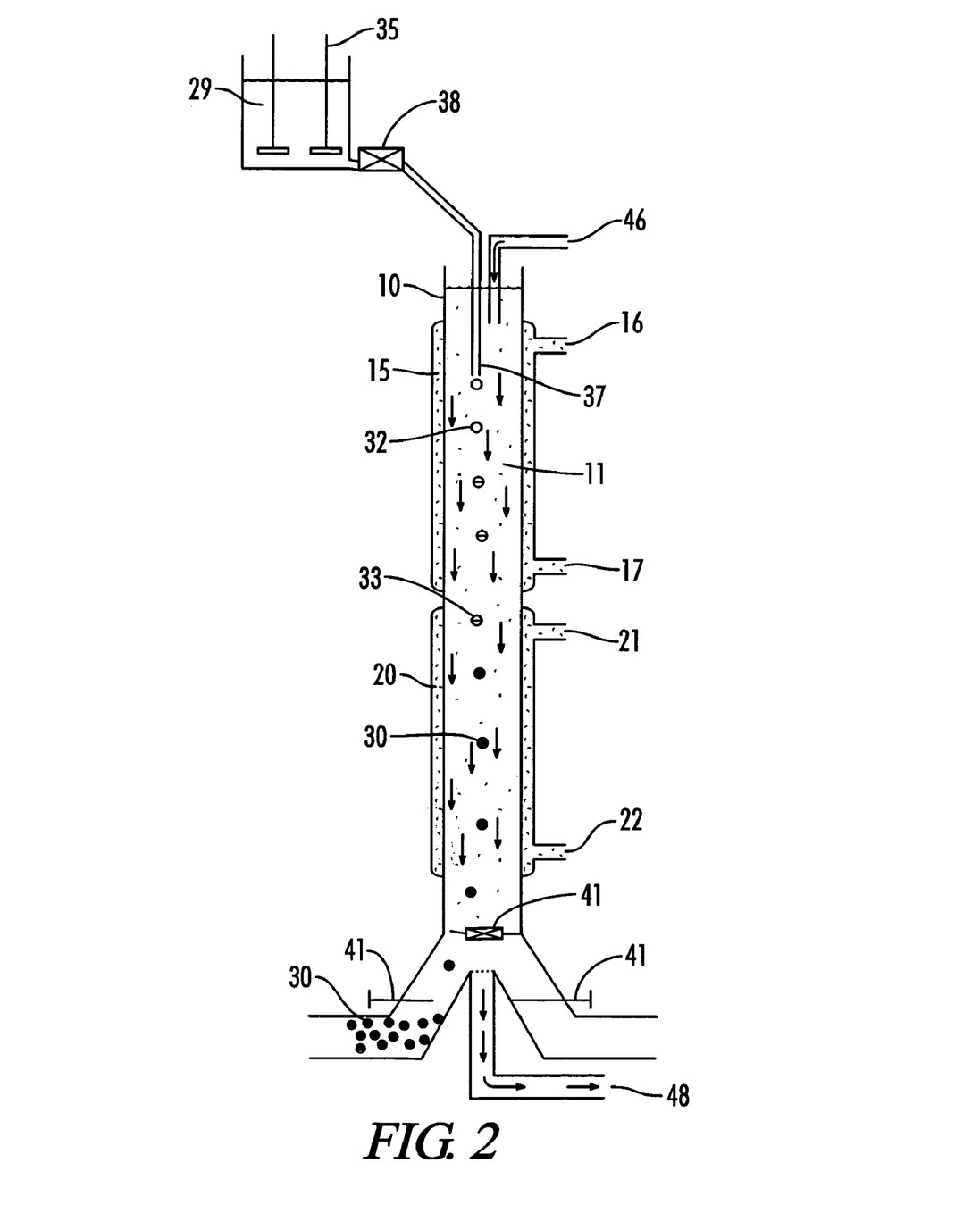
FIG. 2 is a diagrammatic side elevation of an apparatus of FIG. 1 that further comprises a column liquid that flows through the column.
Figure 4:
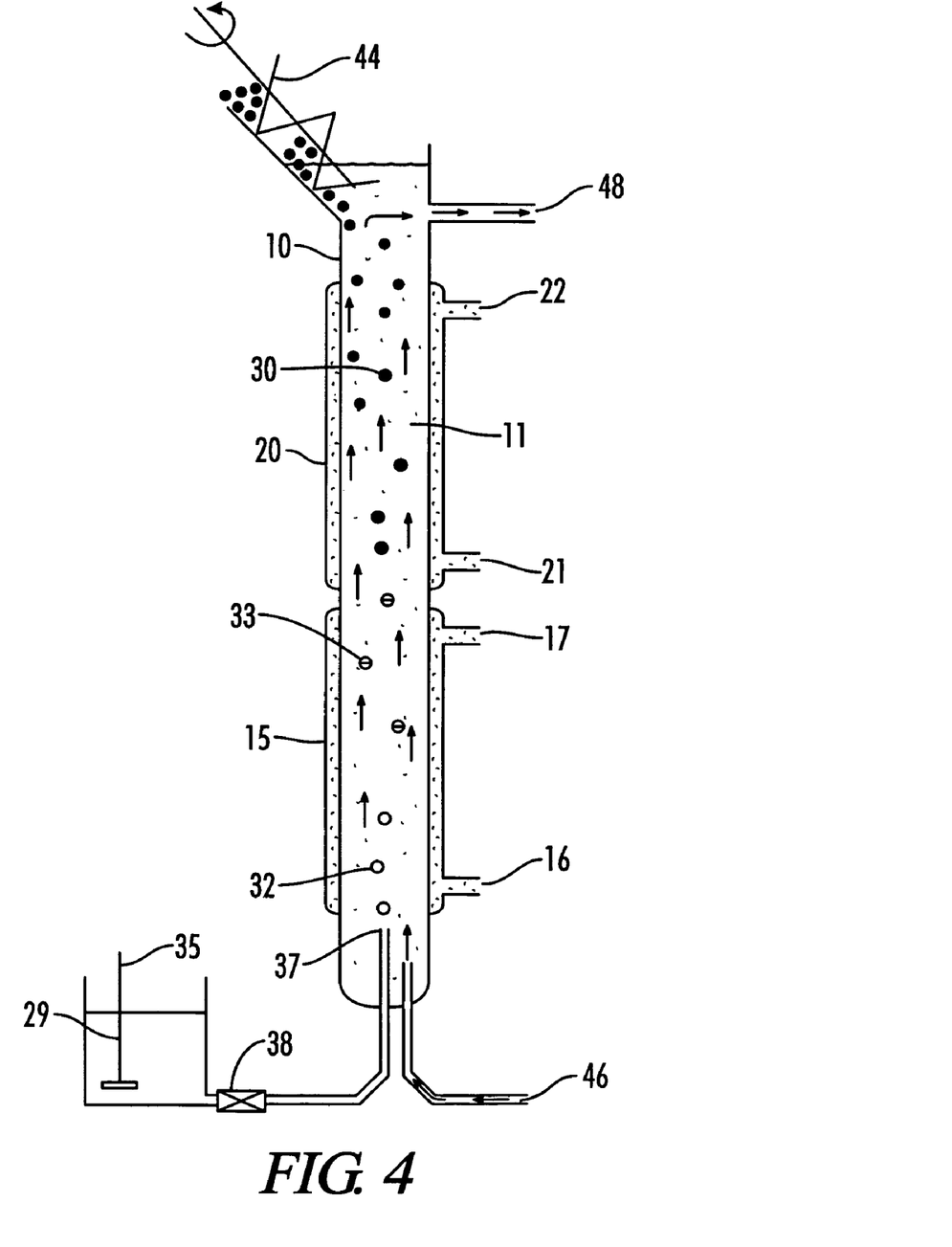
FIG. 4 is a diagrammatic side elevation of an apparatus of FIG. 3 that further comprises flowing column liquid.

In the embodiments of the present invention, including those depicted in FIGS. 2 and 4, the column liquid 11 is circulated throughout a length of the column 10 after entering the column through a column liquid inlet 46 and exiting at outlet 48. This current or flow of the column liquid assists in moving the pellets about the column through the viscous column liquid 11. This allows for the use of a pellet forming medium and column liquid that have similar or the same densities. Additionally, as the column liquid passes the orifice 37, the flow-induced shear of the column liquid acts to pull the droplet of the pellet composition medium sooner that it would have detached in non-flowing column liquid. This effect produces a smaller droplet 32 and smaller resulting pellet 30. Furthermore, one can use the flow of the column liquid to control pellet size by adjusting the fluid velocity. The column liquid may optionally be re-circulated through the column.

The following examples are given for illustration of the present invention, and are not intended to be limiting thereof.

EXAMPLES

Example 1

Matrix: Dexamethasone 10%
PEG base (Mixture of PEG 3350 and PEG 1500) 90%
Liquid in the column: Silicone oil with viscosity of 5 cst.

Example 2

Matrix: Dexamethasone 10%
PEG 3350 80%
Glyceryl dibehenate 10%
Liquid in the column: Silicone oil with viscosity of 5 cst.

Example 3

Matrix: Theophylline 10%
PEG base 80%
Glyceryl pamitostearate 10%
Liquid in the column: Silicone oil with viscosity of 5 cst.

Example 4

Matrix: Active
Glyceryl dibehenate
Liquid in the column: mixture of glycerol:water (70:30)

Example 5

Matrix: Active
Glyceryl dibehenate
Brij 58
Liquid in the column: Propylene glycol.

Example 6

Matrix: Active
HPMC
PEG base
Liquid in the column: Silicone oil with viscosity of 5 cst.

Example 7

Matrix: Active
MCC
Lactose
Carnauba wax
Liquid in the column: Liq. PEG 200.

Example 8

Matrix: Active
Carnauba wax
Liquid in the column: Ethyl alcohol (25%) and water (75%).

Figure 5:
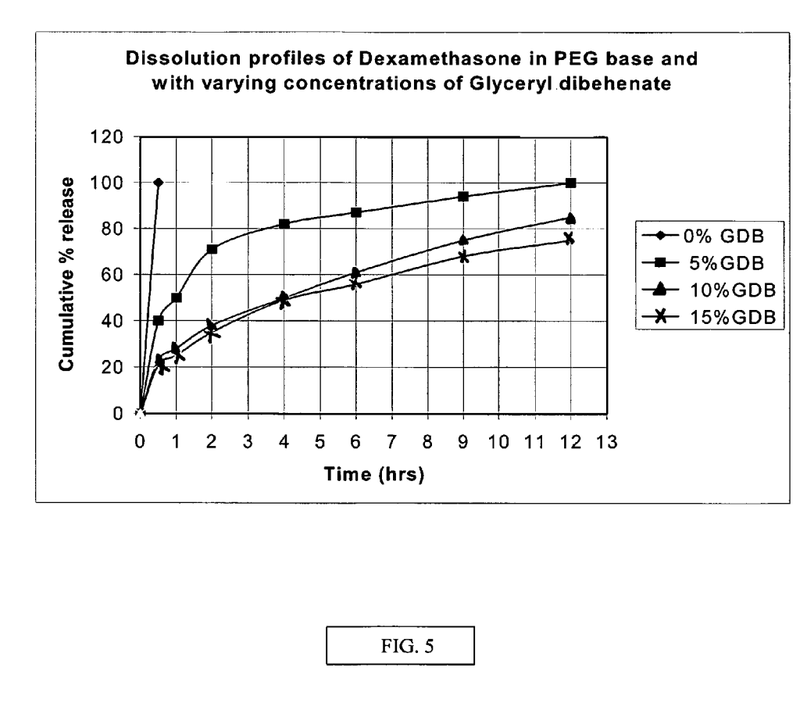
FIG. 5 is a chart showing dissolution profiles of dexamethasone in a PEG base and with varying concentrations of glyceryl dibehenate.
Figure 6:
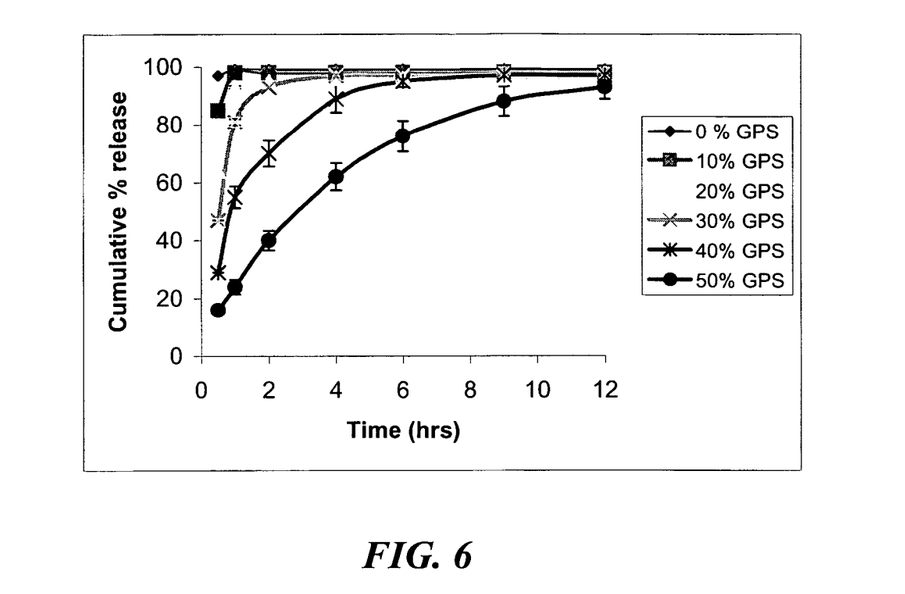
FIG. 6 is a chart showing dissolution of theophylline anhydrous in a PEG base and with varying concentrations of glyceryl palmitostearates.

FIGS. 5 and 6 show the dissolution profiles of dexamethasone and theophylline sustained release pellets, respectively. Dexamethasone is a water insoluble drug and theophylline is a water soluble drug. Using a combination of PEGs and triglycerides, the active release was sustained for a period of 12 hours.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Throughout this application, various publications are referenced. The disclosures of these publications, and the references cited therein, in their entireties are hereby incorporated by reference in their entirety into this application in order to more fully describe the state of the art to which this invention pertains.

Unless otherwise indicated, all numbers expressing quantities of ingredients, properties, amounts, and so forth used in the Specification and Claims are to be understood as being modified in all instances by the term "about." Accordingly, unless indicated by the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental sections or the example sections are reported as precisely as possible. Any numerical value, however, inherently contain certain errors necessarily resulting from the standard deviation found in their respective testing measurements.

We claim:

1. A method of preparing a spherical pellet, comprising:
   providing a pellet forming medium that comprises an active ingredient and a carrier, the carrier comprising a solid material that melts upon heating and encapsulates said active ingredient upon solidification;
   providing a column;
   melting the pellet forming medium to form a liquid pellet forming medium;
   introducing the liquid pellet forming medium into a column liquid that is housed in a column, with the column liquid being maintained at a first temperature throughout a first length of the column and being maintained at a second temperature throughout a second length of the column, the pellet forming medium being at least partially miscible with the column liquid;
   cooling the pellet forming medium in the first and second temperatures so that the pellet forming medium solidifies and forms pellets; and
   separating the pellets from the column liquid.

2. The method of claim 1, wherein the pellet forming medium is introduced drop wise into the column liquid.

3. The method of claim 1, wherein the column liquid is inert to the pellet forming medium and the pellets.

4. The method of claim 1, wherein column liquid is introduced at an inlet port, and removed at an outlet port, and produces a column liquid current across a portion of the column that acts on the pellet forming medium as it travels a length of the column.

5. The method of claim 1, wherein the introducing step comprises introducing the pellet forming medium into the column liquid through an orifice.

6. The method of claim 5, wherein the orifice is a nozzle.

7. The method of claim 5, wherein the orifice is downstream from the column liquid injection port.

8. The method of claim 1, wherein the pellet forming medium comprises at least one of a:
   hydrophilic solid selected from the group comprising polyethylene glycols(PEGs), polyethylene oxide (PEOs), povidone (PVP), polyvinyl alcohol, sugars, water soluble polyoxyethylene derivatives, polyethylene-propylene glycol copolymers(poloxamers), PEG derivatives, PEO derivatives, PEG-PEO derivatives or combinations thereof; and/or a
   hydrophobic solid selected from the group comprising glyceryl monostearate, glyceryl palmitostearate, glyceryl dibehenate, cetostearyl alcohol, cetyl alcohol, stearyl alcohol, cholesterol, hydrogenated vegetable oils, phospholipids and its derivatives, lanolin, lecithin, triglycerides, long chain fatty acids/hydrocarbons, hard fat, oil soluble Brijs, Cocoa butter, waxes or combinations thereof.

9. The method of claim 1, wherein the column liquid comprises at least one of silicone oil, mineral oil, fixed/vegetable oils, fluorocarbon fluids, aliphatic long chain hydrocarbons.

10. The method of claim 1, wherein the column liquid comprises at least one of a liquid polyethylene glycol, propylene glycol, propylene carbonate, glycofural, glycerin, ethyl alcohol, water.

11. The method of claim 1, wherein the liquid pellet forming medium comprises an active ingredient.

12. The method of claim 11, wherein the active ingredient is a pharmaceutical.

13. The method of claim 11, wherein the active ingredient is a fertilizer.

14. An apparatus for producing pellets from a liquid pellet composition, comprising:
   a housing that comprises a liquid pellet forming medium that has at least one active ingredient and molten carrier that encapsulates said active ingredient upon solidification;
   an elongated column for housing column liquid;
   a column liquid, the column liquid being at least partially miscible with the liquid pellet forming medium;
   a first temperature controlling element engaging the column and capable of maintaining a first temperature in the column liquid, the first temperature being above/below the solidification temperature of the liquid pellet composition;
   a second temperature controlling element engaging the column and capable of maintaining a second temperature in the column liquid, the second temperature being lower than the first temperature;
   an injection orifice to introduce the liquid pellet composition to the column liquid; and
   a collection device for removing pellets from the apparatus.

15. The apparatus of claim 14, wherein the temperature controlling element is a temperature controlling jacket.

16. The apparatus of claim 14, wherein the temperature controlling element is a coil that engages the column.

17. The apparatus of claim 14, wherein the column liquid comprises at least one of silicone oil, mineral oil, fixed/vegetable oils, fluorocarbons, aliphatic long chain hydrocarbons, liquid polyethylene glycol, propylene glycol, propylene carbonate, glycofural, glycerin, ethyl alcohol, water.

18. The apparatus of claim 14, further comprising an injection port for injecting column liquid into the column, and a exit port downstream of the injection port, producing a downstream flow for a length of the column in the direction of pellet composition travel.

19. An apparatus for producing pellets from a liquid pellet composition, comprising:
   a housing that comprises a liquid pellet forming medium that has at least one active ingredient and molten carrier that encapsulates said active ingredient upon solidification;
   a column liquid, the column liquid being at least partially miscible with the liquid pellet forming medium;
   an elongated column for housing column liquid, and comprises a column liquid inlet and a column liquid outlet, which together produce a column liquid flow from the inlet to the outlet;
   a first temperature controlling element engaging the column and capable of maintaining a first temperature in the column liquid, the first temperature being above/below a solidification temperature of the liquid pellet composition;
   an injection orifice to introduce the liquid pellet composition to the column liquid for travel along the column liquid flow, the nozzle being downstream of the column liquid inlet and upstream of the column liquid outlet such that the column liquid flows past the injection nozzle; and
   a collection device for removing pellets from the apparatus.

20. The apparatus of claim 19, wherein the cooling element is a cooling jacket.

21. The apparatus of claim 19, wherein the cooling element is a coil that engages the column.

22. The apparatus of claim 19, wherein the column liquid comprises at least one of silicone oil, mineral oil, fixed/vegetable oils, aliphatic long chain hydrocarbons, liquid polyethylene glycol, propylene glycol, propylene carbonate, glycofural, glycerin, ethyl alcohol, water, fluorocarbon fluids.

23. The apparatus of claim 14, further comprising a stirrer in said housing that engages and mixes the liquid pellet forming medium.

24. The apparatus of claim 14, further comprising a pump to deliver the liquid pellet forming medium to the elongated column.

25. The apparatus of claim 14, wherein the injection orifice to introduce the liquid pellet composition to the column liquid is above the surface of the column liquid.

26. The apparatus of claim 18, wherein the injection orifice is located downstream on the injection port.

27. The apparatus of claim 14, wherein the column liquid is stationary.

28. The apparatus of claim 19, further comprising a stirrer in said housing that engages and mixes the liquid pellet forming medium.

29. The apparatus of claim 19, further comprising a pump to deliver the liquid pellet forming medium to the elongated column.

30. The process of claim 1, wherein the melting point of the pellet forming medium is less than about 100 degrees Celsius.

31. The process of claim 1, wherein the pellet forming medium further comprises an excipient.

32. The process of claim 31, wherein the excipient is a release-retarding polymer.

33. An apparatus for producing pellets from a liquid pellet composition, comprising:
- a housing that comprises (i) a liquid pellet forming medium that has at least one active ingredient and molten carrier that encapsulates said active ingredient upon solidification, and (ii) a stirrer in said housing that engages and mixes the liquid pellet forming medium;
- an elongated column for housing column liquid;
- a column liquid;
- a first temperature controlling element engaging the column and capable of maintaining a first temperature in the column liquid, the first temperature being above/below the solidification temperature of the liquid pellet composition;
- a second temperature controlling element engaging the column and capable of maintaining a second temperature in the column liquid, the second temperature being lower than the first temperature;
- an injection orifice to introduce the liquid pellet composition to the column liquid; and
- a collection device for removing pellets from the apparatus.

* * * * *